United States Patent [19]

Raimond

[11] Patent Number: 4,588,422
[45] Date of Patent: May 13, 1986

[54] PROCESS AND EQUIPMENT FOR SAMPLING A GASEOUS EFFLUENT AND THEIR APPLICATION TO CHROMATOGRAPHY

[75] Inventor: Michel Raimond, Mormant, France
[73] Assignee: Elf France, Paris, France
[21] Appl. No.: 558,611
[22] Filed: Dec. 7, 1983
[51] Int. Cl.$^4$ .................... B01D 53/04; G01N 31/08
[52] U.S. Cl. ........................................ 55/67; 73/23.1; 73/864.81
[58] Field of Search .............. 55/67, 197, 386; 73/19, 73/23.1, 864.81; 422/78; 436/161

[56] References Cited

U.S. PATENT DOCUMENTS

| | | | |
|---|---|---|---|
| 3,112,639 | 12/1963 | Maxwell | 73/23.1 |
| 3,171,274 | 3/1965 | Loyd | 73/23.1 |
| 3,283,563 | 11/1966 | Turner et al. | 73/23.1 |
| 3,385,101 | 5/1968 | Roof | 73/23.1 |
| 3,518,059 | 6/1970 | Levy | 55/67 X |
| 3,545,255 | 12/1970 | Levy et al. | 73/23.1 X |
| 3,650,090 | 3/1972 | Temple et al. | 55/67 X |
| 3,807,233 | 4/1974 | Crawford | 73/864.81 X |
| 4,007,626 | 2/1977 | Roof et al. | 73/23.1 |
| 4,057,997 | 11/1977 | Chandler | 73/23.1 |
| 4,234,315 | 11/1980 | Scott | 422/78 X |
| 4,300,393 | 11/1981 | Stearns | 73/864.81 X |
| 4,399,688 | 8/1983 | Dennis | 73/864.81 X |
| 4,409,814 | 10/1983 | Onuma et al. | 73/19 |
| 4,467,038 | 8/1984 | Scott | 436/161 X |

FOREIGN PATENT DOCUMENTS

| | | |
|---|---|---|
| 2063575 | 7/1971 | France . |
| 2206858 | 6/1974 | France . |
| 2456320 | 12/1980 | France . |
| 2515821 | 12/1983 | France . |

Primary Examiner—Robert Spitzer
Attorney, Agent, or Firm—Schwartz, Jeffery, Schwaab, Mack, Blumenthal & Evans

[57] ABSTRACT

The present invention concerns a process and equipment for drawing off a sample for a chromatographic analysis installation. In addition to the chromatographic analysis apparatus 22 per se and a set of rotary pneumatic valves to which it is normally associated, an additional rotary pneumatic valve is connected as follows:
an inlet pipe of the gaseous stream to be analyzed;
two pipes connecting this valve to the first valve of the above-mentioned set of and;
an open-to-air pipe that is associated to means of injecting water vapor and/or drying gas, at counter-current to the flow direction of the open-to-air stream.

5 Claims, 1 Drawing Figure

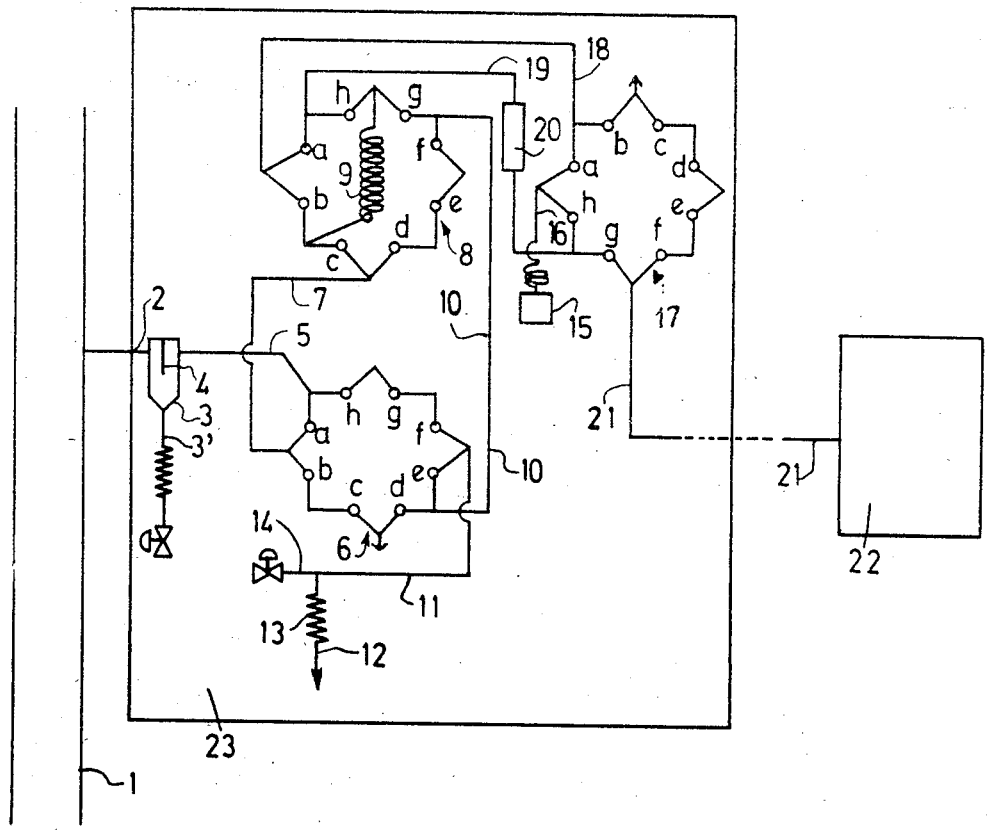

PROCESS AND EQUIPMENT FOR SAMPLING A GASEOUS EFFLUENT AND THEIR APPLICATION TO CHROMATOGRAPHY

FIELD OF THE INVENTION

The present invention concerns an improvement to analysis processes by chromatography of gas and especially of gas containing solid impurities. This improvement applies more particularly to the chromatographic analysis of gaseous effluents such as fumes, and especially fumes issuing from a catalytic cracking unit, containing solid impurities and applies, most particularly, to drawing off samples of the said gaseous effluents with a view to submitting them to analysis by chromatography.

The present invention also relates to an improvement to analysis by chromatography methods allowing the operation of the above-mentioned process and applies more particularly to equipment for drawing off samples from these installations.

DESCRIPTION OF THE PRIOR ART

It is known that the analysis by chromatography of gases and especially fumes necessitates a previous purification treatment of gas or fumes with a view to eliminating, on the one hand, the solid particles carried along and, on the other hand, certain constituents likely to corrode or erode the pipes as well as any trace of humidity. The known processes and installations consequently necessitate supplementary step and equipment for purification, respectively for the elimination of solid constituents (for example, by dust-removing with the use, among others, of filters, electrostatic filters, cyclones), on the one hand, and on the other hand corrosive gaseous constituents (for example, by washing with the use of a base in a suitable scrubber) as well as traces of humidity (water in the vesicular or vaporized form) through passage on an adsorbant mass bed or in a water trap where part of the $SO_2$ present is retained.

The applicant has knowledge of the following U.S. patents constituting the background of the invention. These documents are respectively: U.S. Pat. Nos. 4,234,315, 3,518,059, 3,650,090, 4,057,997. However, none of this prior art can be considered as able to lead to a limitation of the scope of the invention.

The drawbacks of these known processes and installations result from the fact:

that they necessitate apparatus for purifying the gaseous stream to be analysed, thus implying supplementary investment in equipment;

that they necessitate constant surveyance of the various elements of this equipment and especially of the dust-removing elements. Indeed, as untimely blocking of the dust-removing elements or certain pipes (that can, for example, result from an accidental afflux of particles issuing from a throwing out of the catalytic cracking unit) can render the chromatographic analysis impossible whereas it is exactly in the case of such a breakdown that it is important to carry out these analysis, and this in order to intervene on the adjustment of the cracking unit, especially in the case of a totally automatized operation of the catalytic cracking unit.

that the above-mentioned purification leads to a modification of the composition of the fumes, so that the chromatographic analysis is carried out on a gaseous stream that is no longer representative of the composition of the original fumes and thus that the results of the chromatographic analysis are altered. It is obvious that the error that results therefrom is prejudicial to the perfect adjustment of the cracking unit and thus to the correct operation of an automatized installation;

that they lead, on the one hand, to erosion of the pipes of the purification equipment and, on the other hand, due to over long immobility of certain constitutents in the pipes, to corrosion.

SUMMARY OF THE INVENTION

The present invention concerns an improved process and installation for gas analysis by chromatography that allow to eliminate the above-mentioned drawbacks, on the one hand, and, on the other hand, lead to a precision and a reliability of results of the analysis rendering possible the control of a catalytic cracking unit and the automatized operation of such a unit.

This process and installation allow:

to avoid the prior supplementary step and equipment for purification of the gaseous effluent on which it is desired to conduct the chromatographic analysis;

to carry out the analysis on an identical gaseous sample, to within a few solid constituents and slight humidity, of the fumes stream on which the gaseous stream was drawn off;

to obtain an effective analysis of the composition of the fumes and thus to render possible the guiding and the automatic control of a catalytic cracking unit;

to allow the obtention of a sample, purified of solid constituents and traces of humidity, at the immediate proximity to the main fumes evacuation pipe, without necessitating prior cooling of the sampled gaseous stream, and the transmission of the thus purified sample, but having a gaseous composition identical to that of the fumes, to the analysis unit which can be situated in a building other than that where the sampling is carried out;

to necessitate only an extremely simple modification of the chromatography analysis installations and especially of the sample injection equipment in the chromatography analysis unit per se.

The present invention concerns an improved analysis process by chromatography of the gaseous effluents containing solid impurities and, more specifically, a process for drawing off samples of the said gaseous effluents present at a first pressure higher than atmospheric pressure with a view to submitting them to an analysis by chromatography, this process of drawing off samples comprising the following steps:

a first step of sweeping a circuit by a secondary stream of the said gaseous effluents and sending back into the atmosphere the said secondary stream;

a second step of exposing to air a second part of the said circuit comprising a capillary pipe so that the pressure prevailing in this part of the circuit falls to atmospheric pressure, the sweeping being continued in the said first part of the said circuit;

a third step of sweeping the said capillary pipe comprised in the second part of the said circuit by a vector gas issuing from an auxiliary circuit and circulating along a direction contrary to that of the displacement of the secondary stream of the first step, the sweeping being continued in the said first part of the said circuit;

a fourth step of injection of a water vapor stream then of a stream of a drying gas, both at a second pressure higher than the first pressure mentioned above, in the circuit itself of the first step, in a direction contrary to that of the displacement of the secondary stream of the first step, and of the circulation of the vector gas at counter-current to its preceding circulation direction in the said auxiliary circuit.

According to one embodimant of the invention, the different circuits are produced by the use of bimatic pneumatic valves.

According to another embodiment of the invention, the water vapor stream injected in the circuit of the first step, at its exit of the first circuit is sent into a separator in which are separated the solid particles, and thereafter it is sent into the main fumes stream, on which the sampling is carried out.

According to another embodiment of the invention the first three steps have a duration of about 1 to 3% the time of the four steps.

Preferably, the process is operated in a chamber thermoregulated at a temperature of about 150° C.

The present invention also concerns an improved installation for the chromatographic analysis and especially equipment for drawing off samples of a gaseous effluent for the operation of the above-mentioned process.

Such an improved installation between the chromatography analysis apparatus and a set of bimatic pneumatic valves that are normally associated thereto comprises a supplementary bimatic pneumatic valve to which are connected the feed pipe of the gaseous stream to be analysed, two pipes connecting it to the set of valves normally associated to the chromatographic analysis apparatus, and an open-to-air pipe, this open-to-air pipe comprising injection means of water vapor and/or drying gas at counter-current to the flow direction of the open-to-air flow.

Preferably, the open-to-air pipe, downstream of the water vapor and/or drying gas injection means comprises throttling means or a neck.

According to one embodiment of the invention, the feed pipe is provided with a trap for the separation of the solid particles.

Preferably, the said trap comprises a baffled route and an evacuation in tank.

Other aims and advantages of the invention will appear from reading through the following description of a non-limitative embodiment of the invention.

BRIEF DESCRIPTION OF THE INVENTION

The single FIGURE represents a schematic view of the installation according to the invention.

DETAILED DESCRIPTION OF THE INVENTION

The installation according to the invention, represented on the drawing, is connection to an effluents gas pipe 1, for example, of fumes produced by a catalytic cracking unit at a first pressure higher than atmospheric pressure, for example, of about 2 bars and is formed by a circuit comprising a pipe 2, a trap 3 for solid particles and possibly liquid drops comprising an evacuation pipe 3' and a baffled route due to the pressure of a deviation plate 4, a pipe 5 connecting the trap 3 to the gate 6a or 6h of a first bimatic pneumatic valve 6, consisting of a valve at atmospheric pressure, comprising eight gates 6a to 6h, a pipe 7 connecting the first bimatic valve 6 to a second bimatic pneumatic valve 8, also comprising eight gates 8a to 8h, a capillary pipe 9 connecting gates 8c or 8b to gates 8h or 8g, a pipe 10 connecting gates 8g or 8f to gates 6e or 6d and a pipe 11 connecting 6f or 6e to an evacuation pipe 12 comprising a neck or capillary 13, to an injection pipe 14 of water vapor under pressure or drying air under pressure.

This installation is furthermore formed of an auxiliary circuit comprising arrival means 15 of a carrier gas, an arrival pipe 16 of this carrier gas to gates 17a and 17h of a third bimatic pneumatic valve 17, also comprising eight gates, 17a to 17h, a pipe 18 connecting the gates 17a or 17b of the third pneumatic valve 17 to gate 9a or 9b of the second pneumatic valve 9, a pipe 19 connecting gates 9a or 9h of the pneumatic valve 9 to valves 17h or 17g of the pneumatic valve 17, adsorption bed of water 20 placed on the pipe 19 between the two valves 9 and 17, a pipe 21 connecting gates 17g and 17f of the pneumatic valve 17 to a chromatographic analysis apparatus generally represented by reference 22.

In fact, the totality of the installation, with the exception of pipe 1 and apparatus 22, is disposed in a thermally insulated chamber 23, the temperature of which is maintained at a value of about 150° C., the part of the installation thus contained in chamber 23 that constitutes the injection unit of the sample can be placed adjacent to the pipe 1 on which the sample destined to be analysed by chromatography is drawn off. The chromatography analysis apparatus 22 is generally positioned in the analysis unit situated in another building.

The operation of the installation thus represented implies four phases.

Phase 1

The gates 6a, 8c, 8g and 6e are open. The other gates are closed.

The opening of gates 6a, 8c, 8g provokes the passage of a secondary stream of fumes in pipe 2. A part of the solid impurities present in this stream falls to the bottom of trap 3. The secondary stream of fumes, still bearing a part of the solid impurities, passes by gates 6a, 8c, 8g, 6e and by pipes 5, 7, 9, 10, 11, 12 to be rejected into the atmosphere. The pressure prevailing in these pipes and which forms the first pressure indicated above during the passage of this secondary stream is about 2 bars.

Phase 2

6h, 6g, 6f, on the one hand and gates 6b, 8c, 8g, 6d, on the other hand, are open. The closing of gates 6a and 6e and the opening of gates 6h, 6g and 6f causes the secondry stream of fumes to be sent into pipe 11 and and rejected into the atmosphere. The residual stream of the secondary stream of fumes ceases to flow in pipes 7, 9 and 10 due to the fact that the opening of the gates 6b, 8c, 8g, 6d causes these pipes to be brought back to atmospheric pressure.

The solid impurities present in the residual stream due to the reduction in pressure fall to the bottom of the different pipes. In this phase 2, 17a, 8a and 17g are also open. The carrier gas circulates in pipes 16, 18 and 19.

Phase 3

Gates 6h, 6g and 6f are open, on the one hand, and, on the other hand, gates 17a, 8b, 8h and 17g are open. By gates 6h, 6g and 6f, the secondary stream of fumes is sent into pipe 11 and rejected into the atmosphere. The carrier gas arriving through pipe 18 and gate 8b carries along the part of the residuary stream of fumes purified of solid particles present in the capillary pipe 9, in pipe 19, in an adsorption bed 20, where the water contained in the fumes stream is eliminated by adsorption, then by gate 17g and pipe 21 towards apparatus 22 for chromatographic analysis.

Phase 4

Gates 6e, 8g, 8c, 6a are open, on the one hand, as well as, on the other hand, gates 17h, 8a, 17b.

The water vapor under pressure of 4 bars is injected through pipe 14; part of the water vapor escapes into the atmosphere through pipe 12, neck or restriction 13 preventing the whole of the injected water vapor to escape through pipe 12. The water vapor is thus brought through pipe 11 towards the pneumatic valve 6 and travels through pneumatic valves 6 and 8 exactly the same route as that taken by the secondary stream of fumes during Phase 1, In fact, the water vapor stream thus injected sends back the solid impurities and other traces of gaseous impurities left in the corresponding pipe-lines and valves towards the atmosphere through pipe 3' so as to carry along the solid and possibly liquid impurities that are disposed in the bottom of the trap 3.

Once the trap is emptied of the impurities that it contains the water vapor is sent back by pipe 2 towards the fumes pipe 1. The arrival of the vapor stream under pressure of 4 bars is injected by pipe 14 in order to follow the same route as that previously followed by the water vapor stream under pressure. The corresponding parts of the installation were thus dried.

Furthermore, in the auxiliary circuit, by pipes 18 and 19 and gates 17h, 8a and 17b the carrier gases pass along an identical route to that followed in phase 3, but in a contrary direction, the carrier gas, being rejected into the atmosphere.

By way of example of embodiment of the invention, the gaseous stream circulating in the pipe 1 is formed of fumes at a temperature of about 800° C. issuing from a catalytic cracking unit known as F.C.C. is at a pressure of 2 bars and presents the following composition:

$O_2$: 3.5%
$CO_2$: 12%
$SO_2$: 1%
CO: 1000 ppm
$H_2O$: traces
dust: traces
$N_2$: qsp 100

Every 8 minutes, a chromatographic analysis must be carried out on a sample drawn off this gaseous stream.

During the first step described herein-above, the gaseous sample is carried out by the pipe 2; the gaseous stream firstly passes into trap 3 wherein a first part of the solid impurities are separated falling to the bottom of the trap, then passes into a circuit formed by pipes 5, 7, 10 and 11 to be rejected into the atmosphere. The duration of this first step is 5 seconds.

The second step comprises the continuation of the circulation of the gaseous stream in a first part of the circuit comprising pipes 5 and 11, on the one hand, and, on the other hand, the exposition to air of the second part of the circuit comprising pipes 7 and 10 and a capillary pipe 9. The duration of this second step is 3 seconds maximum.

The third step comprises the continuation of the circulation of the gaseous stream in the said first part of the circuit comprising the pipes 5 and 11, the sweeping of the capillary pipe 9 by a carrier gas, for example, nitrogen brought by the pipe 18 and sent to the chromatography apparatus 22 by pipe 19, a previous drying being carried out in the adsorption bed 20. The duration of this step is one second. In fact, it can be considered that this third step is combined with the following step 4.

The fourth injection step of water vapor under pressure of 4 bars by pipe 14, at counter-current to the direction previously followed by the gaseous stream, this gaseous stream being displaced in the circuit followed by the gaseous stream during the first step, but in the opposite direction by pipes 11, 10, 7, 5 and 3, firstly, then 11, 10, 7, 5 and 2. Thereafter, the water vapor stream is shut down and is injected by pipe 14 a stream of drying air at a pressure of 4 bars that circulates in pipes 11, 10, 7, 5 and 2 in order to be reinjected into pipe 1.

Of course, the present invention is not limited to the embodiment described and represented but can be adapted to numerous variants available to the man skilled in the art, without departing from the scope and spirit of the invention. Thus, whatever the bimatic pneumatic valves used and especially valves 6 and 8, or 8 gate valves, sold by the Italian Company Carlo Erba under the denomination GR8/A. It is quite obvious that other types of valves, for example, 6 gate valves can be used. It should be noted that the assembly formed by pneumatic valves 9, 17 and the chromatographic analysis apparatus per se 22 constitutes a classic chromatographic equipment and that pneumatic valve 6 and the injection pipe 14 constitute the contribution of the invention to this equipment.

The process and the equipment according to the present invention can be operated on any gaseous effluent carrying along solid impurities but are particularly applicable to the treatment of hot gaseous and corrosive effluents issuing from a catalytic cracking unit called FFC.

I claim:

1. A process for drawing off a sample of a main gaseous effluent stream containing solid particles for chromatographic analysis, said main gaseous effluent stream being at a first pressure higher than atmospheric pressure, said process comprising the following steps:
   (a) forming a secondary stream of said gaseous effluent;
   (b) sweeping a first part of a circuit comprising a capillary tube by said secondary stream of said gaseous effluent, and discharging said secondary stream to the atmosphere;
   (c) connecting said first part of the circuit to atmosphere to bring the pressure of the entire first part of the circuit to atmospheric pressure, and discharging said secondary stream to the atmosphere through a second part of the circuit;
   (d) sweeping said capillary tube by a carrier flowing from an auxiliary circuit in the same direction as that of the secondary stream in step (b), the discharge of said secondary stream being continued through said second part of the circuit;
   (e) injecting a stream of steam followed by a drying gas stream into said first part of said circuit at a second pressure higher than said first pressure in the first part of said circuit, and in a direction opposite to that of the secondary sweeping stream of step (b), said carrier gas circulating in a direction opposite to that of its previous circulation in said auxiliary circuit.

2. A process according to claim 1, wherein the steam is injected into the first part of the circuit at an exit of the first part of the circuit and is sent into a separator wherein solid particles are separated, then is sent into the main gaseous effluent stream on which the secondary stream was drawn off.

3. A process according to claim 1, wherein steps (b), (c) and (d) have a duration period of about, 1 to 3% of the time of step (e).

4. A process according to claim 1, wherein the process is carried out in a thermoregulated chamber at a temperature of about 150° C.

5. A process according to claim 1 wherein main gaseous effluent stream is gaseous effluent from a catalytic cracking unit.

* * * * *

UNITED STATES PATENT AND TRADEMARK OFFICE
CERTIFICATE OF CORRECTION

PATENT NO. : 4,588,422
DATED : May 13, 1986
INVENTOR(S) : Michel RAIMOND

It is certified that error appears in the above-identified patent and that said Letters Patent is hereby corrected as shown below:

In the Title Page, Item [21], "558,611" should read --558,811--.

Signed and Sealed this

Twenty-ninth Day of July 1986

[SEAL]

Attest:

DONALD J. QUIGG

Attesting Officer

Commissioner of Patents and Trademarks